(12) United States Patent
Berend et al.

(10) Patent No.: US 10,687,947 B2
(45) Date of Patent: Jun. 23, 2020

(54) AUGMENTS AND METHODS FOR IMPLANTING HIP PROSTHESES

(71) Applicant: Biomet Manufacturing, LLC, Warsaw, IN (US)

(72) Inventors: Keith R. Berend, Columbus, OH (US); Jacob Macke, Warsaw, IN (US)

(73) Assignee: Biomet Manufacturing, LLC, Warsaw, IN (US)

( * ) Notice: Subject to any disclaimer, the term of this patent is extended or adjusted under 35 U.S.C. 154(b) by 106 days.

(21) Appl. No.: 15/977,360

(22) Filed: May 11, 2018

(65) Prior Publication Data

US 2018/0325673 A1 Nov. 15, 2018

Related U.S. Application Data

(60) Provisional application No. 62/506,175, filed on May 15, 2017.

(51) Int. Cl.
*A61F 2/30* (2006.01)
*A61F 2/34* (2006.01)
*A61F 2/46* (2006.01)

(52) U.S. Cl.
CPC ...... *A61F 2/30749* (2013.01); *A61F 2/30724* (2013.01); *A61F 2/30734* (2013.01); *A61F 2/34* (2013.01); *A61F 2002/3085* (2013.01); *A61F 2002/30449* (2013.01); *A61F 2002/30736* (2013.01); *A61F 2002/30784* (2013.01); *A61F 2002/30841* (2013.01); *A61F 2002/4631* (2013.01)

(58) Field of Classification Search
CPC ............... A61F 2/30724; A61F 2/30734; A61F 2002/30736; A61F 2/34; A61F 2002/4631
See application file for complete search history.

(56) References Cited

U.S. PATENT DOCUMENTS

| 4,285,071 A * | 8/1981 | Nelson ............... A61F 2/30724 606/92 |
| 4,563,778 A * | 1/1986 | Roche ...................... A61F 2/34 623/22.38 |
| 5,282,861 A | 2/1994 | Kaplan |

(Continued)

FOREIGN PATENT DOCUMENTS

FR 2707479 A1 * 1/1995 ......... A61B 17/8802

OTHER PUBLICATIONS

Levine, Brett R, et al., "Experimental and clinical performance of porous tantalum in orthopedic surgery", Biomaterials, (27), (Sep. 2006), 4671-81.

*Primary Examiner* — David H Willse
*Assistant Examiner* — Javier G Blanco
(74) *Attorney, Agent, or Firm* — Schweman Lundberg & Woessner, P.A.

(57) ABSTRACT

A method of securing an orthopedic hip prosthesis to an acetabulum of a living being. The prosthesis can be a shell or a cup, and the surgery can be a total hip arthroplasty such as a revision total hip arthroplasty. In some examples the method can include placing an augment at a bone surface of the acetabulum, applying a layer of fixation material over the bone surface in an amount sufficient to cover the augment, and then implanting the prosthesis over the layer of fixation material to secure the prosthesis to the layer of fixation material. In various aspects of the method, the augment can be an anchor or a spacer.

7 Claims, 12 Drawing Sheets

(56) References Cited

U.S. PATENT DOCUMENTS

| | | | |
|---|---|---|---|
| 8,728,168 B2* | 5/2014 | Hanssen | A61F 2/36 623/22.24 |
| 2005/0080490 A1* | 4/2005 | Bertram, III | A61B 17/8808 623/22.28 |
| 2007/0129809 A1* | 6/2007 | Meridew | A61F 2/36 623/22.32 |

* cited by examiner

AUGMENTS AND METHODS FOR IMPLANTING HIP PROSTHESES

CLAIM OF PRIORITY

This application claims the benefit of U.S. Provisional Patent Application Ser. No. 62/506,175, filed on May 15, 2017, the benefit of priority of which is claimed hereby, and which is incorporated by reference herein in its entirety.

TECHNICAL FIELD

This document pertains generally, but not by way of limitation, to augments and methods for implanting orthopedic devices. The augments can include anchors and spacers to be used with acetabular implants for total hip arthroplasty, including revision total hip arthroplasty.

BACKGROUND

A total hip arthroplasty (THA) procedure can be performed to repair a diseased or damaged hip joint and replace it with a hip prosthesis. Sometimes, as with any other mechanical device, a total hip replacement can be subject to various forms of mechanical or biological issues. When issues occur, a reoperation of the hip replacement can be necessary to resolve the issues. Such a reoperation of a THA is called a revision THA. This is usually done several years after the original implantation and is more common in patients who had the initial THA performed at a young age and the patient chose to have a very active physical lifestyle.

One of the challenges of a revision THA is how to securely implant the hip prosthesis, and in particular, how to securely implant an acetabular cup or shell of the prosthesis into the remaining bone of the patient, especially in the presence of poor bone quality or bone loss. Another challenge is achieving a uniform fixation material thickness (e.g., bone cement mantle thickness) between the prosthesis and the bone.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various examples discussed in the present document.

DETAILED DESCRIPTION

Figure 1:
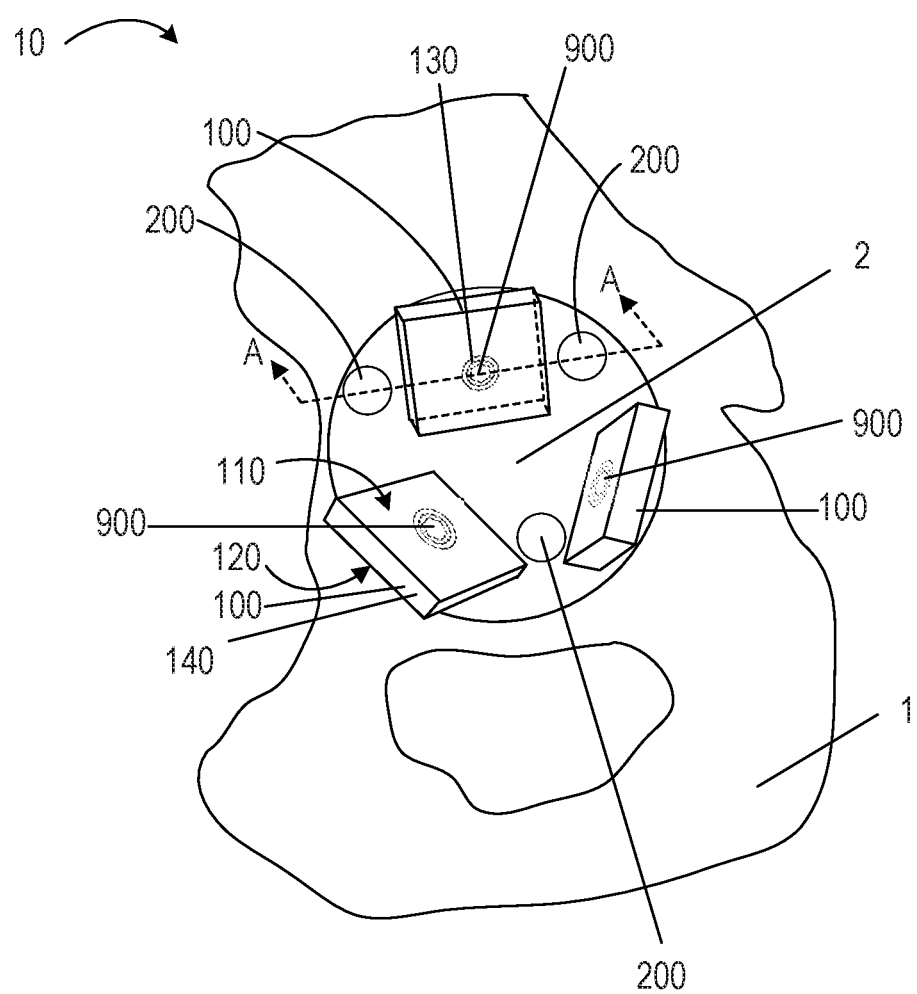
FIG. 1 is a perspective view of illustrative augments including anchors and spacers that are arranged proximate a portion of a hip bone, in accordance with at least one example.

As discussed above, one of the challenges of a total hip arthroplasty (THA), and especially in a revision THA, is how to securely implant the hip prosthesis. It can be difficult to secure an acetabular revision shell of the prosthesis into the remaining bone of the patient, especially in the presence of poor bone quality or bone loss. A second related challenge is how to achieve a uniform thickness of a fixation material (e.g., cement mantle thickness) between the prosthesis and the bone. Conventional methods that rely on the presence of substantially good bone may not be able to provide as strong of an attachment as desired when the patient has poor bone quality or bone loss. The present disclosure addresses these challenges through the use of augments in the form of anchors and spacers, and methods of using these augments to implant a prosthesis.

To improve the quality of the implantation of the prosthesis to the bone when the patient has poor bone quality or bone loss, the present disclosure includes a method of recreating the acetabulum. Recreating the acetabulum is accomplished by securing augments in the form of anchors to good bone, and then applying a layer of fixation material (e.g., a bed of cement) over the anchors and behind a shell or cup of the prosthesis that is physiologically oriented in the acetabulum. This method of recreating the acetabulum can eliminate the need for an expensive revision shell and permit a cup to be directly implanted over the layer of fixation material.

To solve the second challenge of achieving a target fixation material thickness, some conventional acetabular shells incorporate integral spacers therein. However, this limits the surgeon to using the fixation material thickness dictated by the integral spacers. The integral spacers do not provide the surgeon with the option to tailor the fixation material thickness between the bone and the shell of the prosthesis. Variables including patient anatomy, quality of the bone, bone loss and surgeon preferences may result in the surgeon wanting to adjust the fixation material thickness irrespective of the particular shell being used, or to control or adjust the thickness in a uniform or a variable manner across the acetabulum. In shells that incorporate integral spacers, adjusting the thickness in any manner is difficult, if not impossible.

To improve the fixation material thickness control and provide adjustability to the surgeon, the present disclosure includes a method of using augments in the form of spacers that allow the surgeon to adjust and control (e.g., variably or uniformly) the thickness of the fixation material that helps secure the prosthesis to the bone. In general, achieving a target thickness of the fixation material is accomplished by applying a layer of fixation material to the acetabulum, inserting one or more spacers into the cement, and inserting a shell or cup of the prosthesis into the acetabulum until it bottoms out on the spacers.

The anchors, spacers and methods described herein help to correctly orient a shell or a cup in an acetabulum, simplify revision surgeries and reduce operating time. The anchors, spacers and methods can also allow cemented cups, including poly, ceramic and metal dual mobility cups, to be directly implanted in the acetabulum without the shell. This can eliminate the need for expensive acetabular shells altogether. The various anchors, spacers and methods described herein can be used alone or together.

FIG. 1 is a perspective view of a hip bone 1 including illustrative augments (e.g., 100, 200) arranged at am implant site 10 proximate a portion of the hip bone 1, in accordance with at least one example. To solve the challenge of securely implanting a hip prosthesis in the situation where the patient suffers from poor bone quality or bone loss, one or more augments, such as an anchor 100 can be secured to the bone 1 with a fastener 900. FIG. 1 shows three such anchors 100, although any number of anchors 100 may be provided, including a single anchor 100, as will be described below for clarity.

As shown in FIG. 1, the anchor 100 can include a body having a first surface 110 and a second surface 120 opposite and spaced apart from the first surface 110. A third surface 140 can extend from the first surface 110 to the second surface 120 (as shown in the cross-section of FIG. 2C). The anchor 100 can also include an opening 130 (FIG. 2A) extending from the first surface 110 to the second surface 120. The opening 130 can be sized and shaped to accept insertion of a fastener 900 through the opening 130 so that the fastener 900 can be secured to the hip bone 1 (e.g., the acetabulum 2 and surrounding bone). All or a portion of the anchor 100 can be formed of a layer of porous material that promotes boney ingrowth. While the anchor 100 in FIG. 1 is depicted as being generally planar or cuboid shaped, the anchor 100 can take on other forms and features, including but not limited to the example anchors of FIGS. 4, 5A, 5B, 6A, 6B, 7A, 7B, 8A and 8B, which will be described in further detail below. Additional details of the anchor 100 and other anchors will be described in further detail following a description of illustrative methods of using the anchor 100.

Also with reference to FIG. 1, to solve the second challenge of controlling fixation material thickness, one or more augments in the form of a spacer 200 can be provided. The spacer 200 can be a spherical spacer 200 (e.g., a substantially spherical spacer) that is inserted in a layer of fixation material 50 to control a thickness 52 (FIG. 2E). FIG. 1 shows three such spacers 200, although any number of spacers 200 may be provided, including a single spacer 200.

While the anchors 100 and the spacers 200 are shown used together in FIG. 1 and an illustrative method of FIGS. 2A-2E, the anchors and spacers can also be used independent of one another. For example, one or more anchors 100 can be used separately or together with one or more spacers 200, in any number and combination.

Additional details of the spacer 200 will be described in further detail following a description of illustrative methods.

An illustrative method 300 of securing a shell or cup of an orthopedic hip prosthesis 60 to a hip bone 1 using augments such as the anchors 100 and spacers 200 shown in FIG. 1, will be described with reference to FIGS. 2A-2E and FIG. 3.

FIGS. 2A-2E show cross-sectional views, as taken along line A-A' in FIG. 1, of steps of the method 300. FIG. 3 includes an illustrative flow chart outlining the steps of the method 300 depicted in FIGS. 2A-2E, in accordance with at least one example.

Figure 2A:
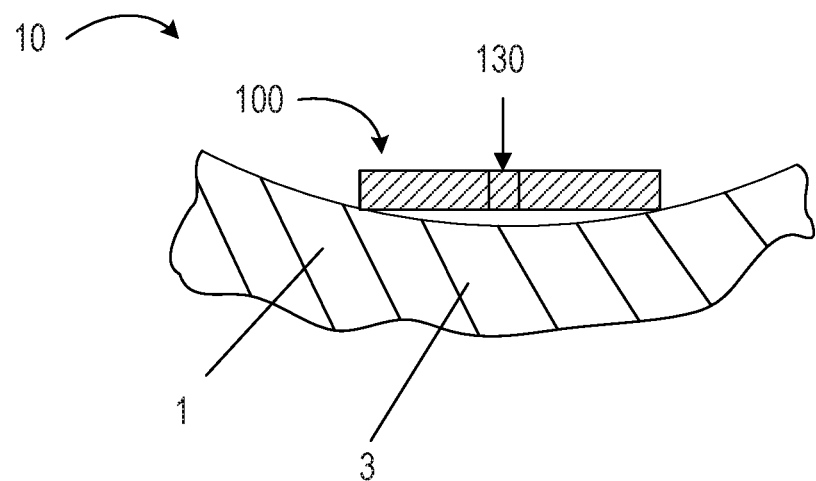
FIGS. 2A-2E are cross-sectional views as taken along line A-A' in FIG. 1, the views illustrate steps of an illustrative method of securing an orthopedic hip prosthesis to a bone of a living being, in accordance with at least one example.
Figure 2B:
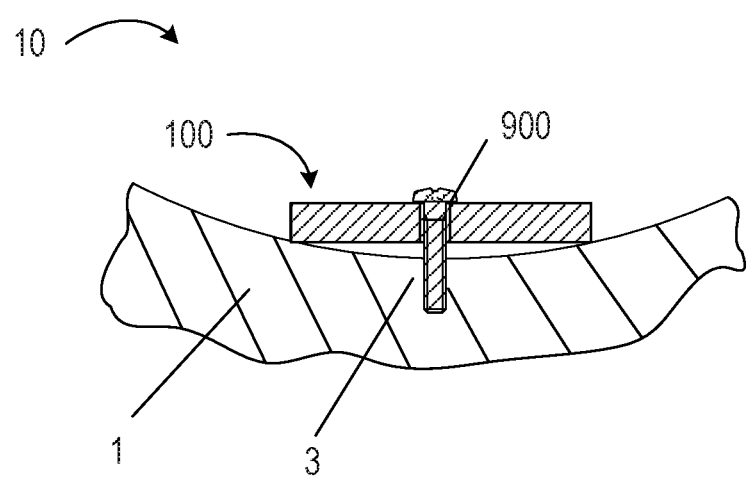
Figure 3:
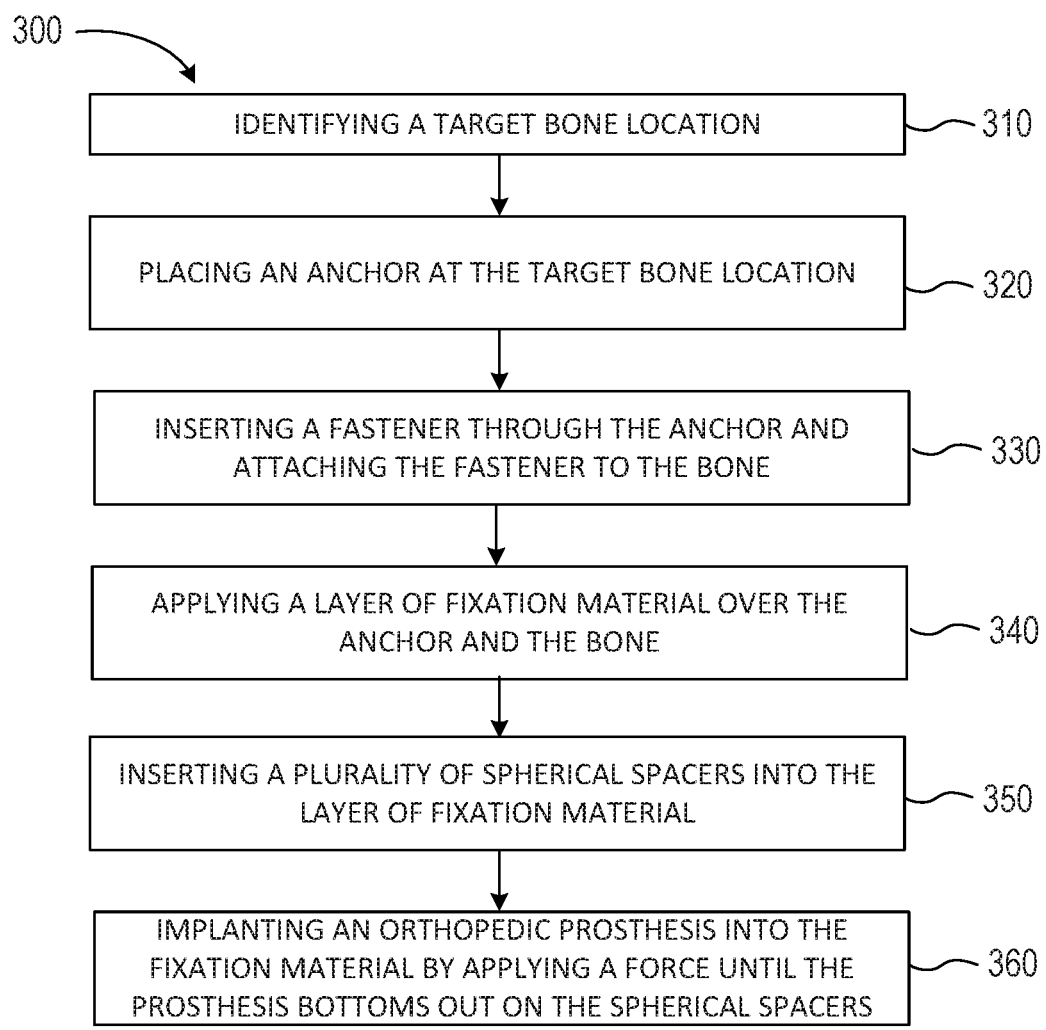
FIG. 3 is a flow chart illustrating a method of securing an orthopedic prosthesis to a bone, in accordance with at least one example, including the example method of FIGS. 2A-2E.

As shown in FIG. 2A, the method 300 can include placing an augment such as anchor 100 at a bone 1. The bone may include a surface of an acetabulum 2. Step 310 can include the surgeon identifying and selecting a target bone location 3 for placing the anchor 100 by determining what portion of the bone 1 is strong enough to support the prosthesis 60 and the functional loads it will incur. Step 310 may include identifying good bone that will serve as the target bone location 3. Identifying good bone may be done by visual identification during surgery or by an analysis of imaging data obtained on the patient. As shown in FIG. 2B, step 320 can include placing the anchor 100 at the target bone location 3. Step 330 can also include inserting a fastener 900 through an opening 130 in the anchor 100 and attaching the fastener 900 to the good bone at the target bone location 3 in order to secure the anchor 100 to the bone 1. In some examples, this area of good bone that makes up the target bone location 3 can be adjacent to areas of poor or missing bone.

Figure 2C:
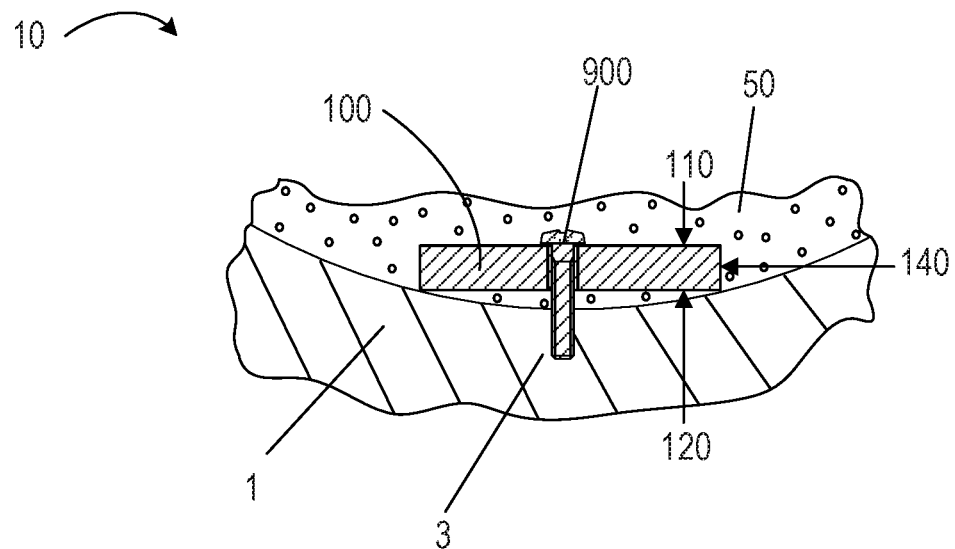

As shown in FIG. 2C, once the anchor 100 is secured to the target bone location 3, step 340 can include the surgeon applying a layer of fixation material 50, such as a bone cement, over the anchor 100 and the bone surface in an amount sufficient to cover the anchor 100. In some examples, the exposed surface area of the anchor 100 that is not attached to the bone 1 is covered (e.g., completely covered, substantially completely covered) by the fixation material 50. A sufficient amount of fixation material can be described as a layer of fixation material 50 that is at least as thick as the thickness of the anchor 100. In some preferred examples, a sufficient amount of fixation material can be described as layer of fixation material 50 that is thicker than a thickness of the anchor 100. The thickness of the anchor 100 can be described as the distance from the first surface 110 of the anchor 100 to a second surface 120 of the anchor 100. In some examples this may be the maximum thickness of the anchor 100. In some examples the layer of fixation material 50 forms a surrogate bone surface for the target bone location 3 and/or bone surrounding the target bone location 3. This surrogate bone surface can provide a stronger attachment of the prosthesis 60 to the bone 1 than if the prosthesis 60 was attached to the bone 1 alone.

Steps 310, 320, 330 and 340 can be repeated as desired to secure additional anchors 100 to the bone 1 and cover the anchors 100 with the fixation material 52. Once the desired number of anchors 100 are attached and sufficiently secured to the bone 1 and the fixation material 50 is layered over the anchor 100 and the bone 1, the prosthesis 60 can be implanted over the fixation material 50 (e.g., skip step 350 and go to step 360).

Alternatively, if it is desired to control a target thickness 52 of the fixation material 50, step 350 can include placing another type of augment, such as a spacer, at the bone 1 surface to facilitate controlling a target thickness 52 of the fixation material 50, before implanting the prosthesis 60 over the fixation material 50.

Figure 2D:
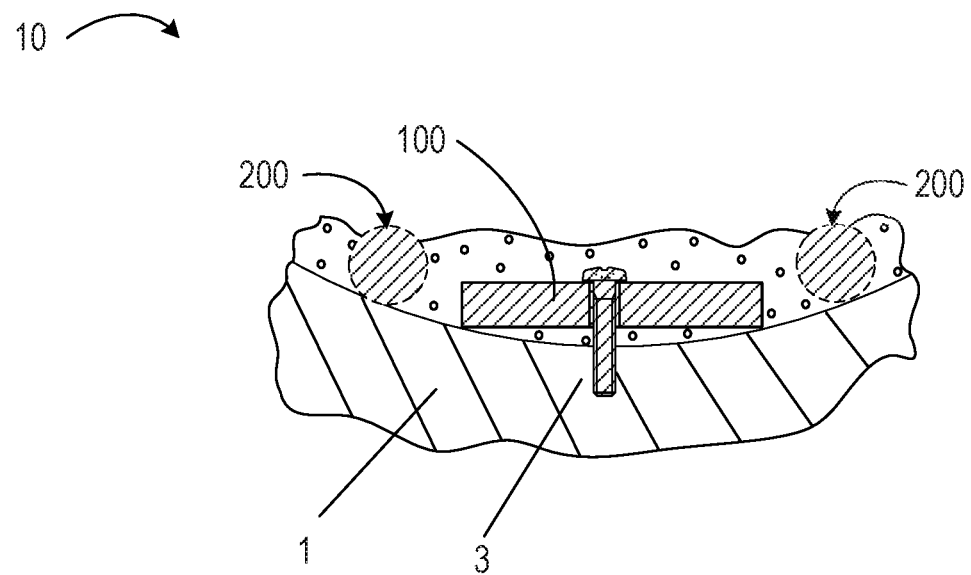
Figure 2E:
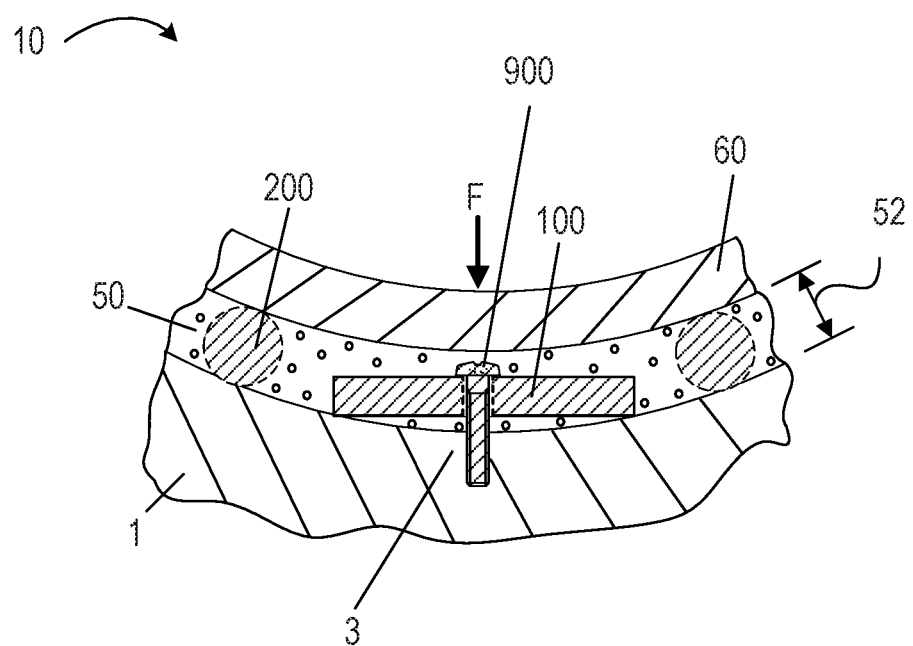

As shown in FIG. 2D, the augment used in step 350 can be one or more of the substantially spherical spacers 200 of FIG. 1. In some examples, a single spacer 200 can be used, but as shown in the example of FIG. 1, three spacers 200 can be provided in a spaced apart relationship to help in properly orienting the shell or cup of the prosthesis 60 to the acetabulum 2. This spaced apart relationship can be a triangular relationship as shown. The spacers 200 are not limited to being used as a set of 3 spacers. Other numbers and arrangements of spacers 200 can also be used, such as one or more, a plurality, or three or more.

As shown in FIG. 2D, step 350 can include inserting the one or more substantially spherical spacers 200 into the layer of fixation material 50. In at least one example, the layer of fixation material 50 should be at least as thick as, or thicker than, the diameter of the spacers 200. The spacers 200 provide control or guidance for achieving a target thickness (e.g., 52, FIG. 2E) of the fixation material 50. Step 360 can include implanting the orthopedic prosthesis 60 into the fixation material 50 by orienting the shell or cup of the prosthesis 60 at the implantation location (e.g., acetabulum 2) and applying a force until the prosthesis 60 bottoms out on the spacers 200 (FIG. 2E). In other words, when the prosthesis 60 is fully seated, the spacers 200 should be contacting both the bone 1 surface and the prosthesis 60 surface, and the gap (e.g., 52) between the bone 1 surface and the prosthesis 60 surface can be occupied by the fixation material 50 (e.g., substantially or completely filled with the fixation material). This is beneficial because the surgeon is able to determine when the prosthesis 60 is fully seated because the prosthesis 60 will not move any further. The surgeon can also be able to visually determine that enough fixation material has been provided by the movement of excess fixation material 50 being secreted out of the gap between the acetabulum 2 and the prosthesis 60. In other words, the surgeon is able to determine that the gap is filled with fixation material. Furthermore, over-seating of the prosthesis, where the surgeon displaces an excessive amount of fixation material 50, which can result in a smaller fixation material 50 thickness 52 than was intended, can also be prevented. The illustrative method 300 reduces challenges in conventional methods where there is no spacer and setting the fixation material 50 thickness 52 is a blind operation for the surgeon. Method 300 also provides more customization options for the surgeon to tailor the fixation material 50 thickness 52.

In some examples of the method 300, the surgeon may attempt to achieve a uniform or substantially uniform target thickness 52 of the fixation material 50. In other examples, the surgeon may intentionally attempt to achieve a variable target thickness 52. In some situations, the surgeon may simply not be able to achieve a uniform target thickness 52 due to variations in the bone 1 surface or the prosthesis 60. This can lead the surgeon to create a variable target thickness 52. In some examples, the target thickness 52 at or around a particular bone location that the spacer 200 is placed, can correspond to a diameter (e.g., 210 a, FIG. 10) of the spacer 200. Controlling or adjusting the target thickness 52 (e.g., FIG. 2E), can include providing guidance, via the spacers 200, in an attempt to achieve the target thickness 52 of the fixation material 50 at the spacers 200, around the spacers, or across the acetabulum 2 (FIG. 1).

Figure 4:
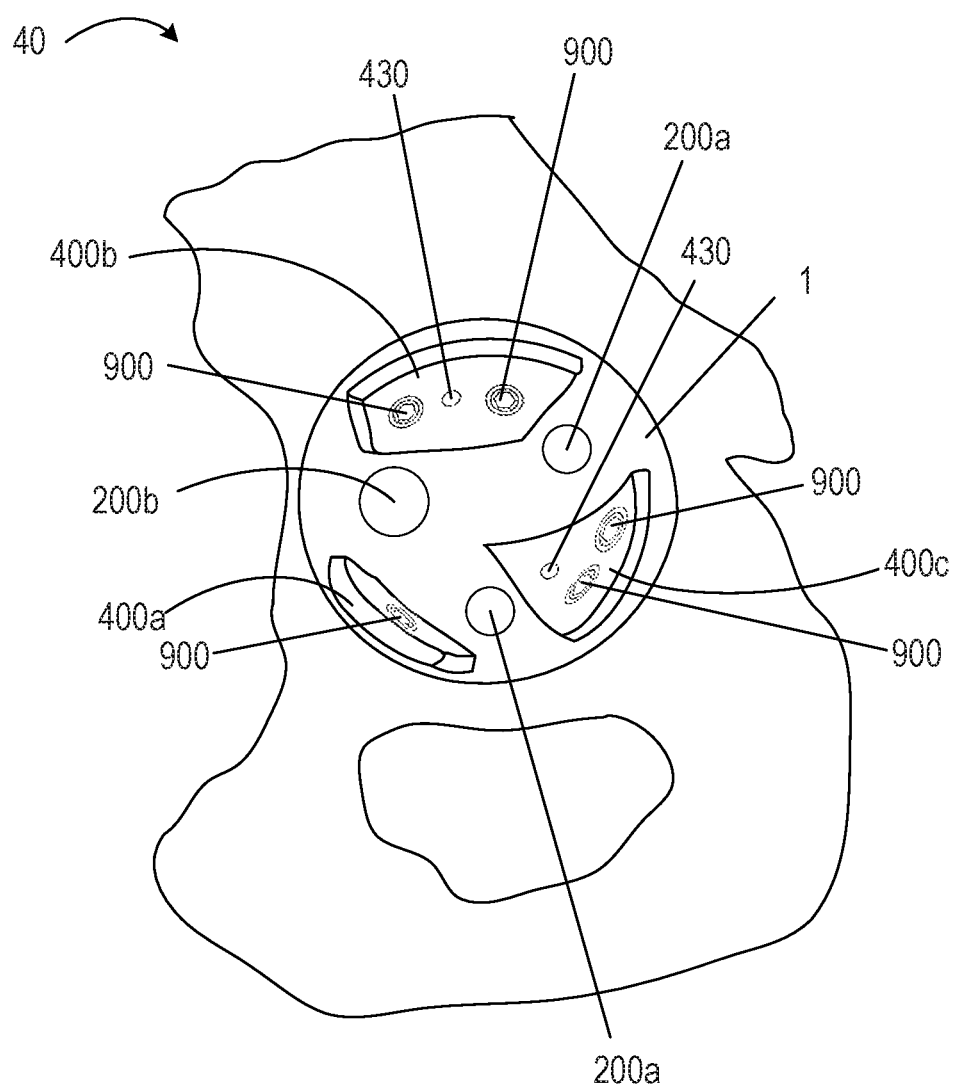
FIG. 4 is a perspective view of another illustrative example of augments arranged proximate a portion of a hip bone, in accordance with at least one example.

In some examples of the method 300, the surgeon may intentionally try to achieve a variable target thickness 52 by using different sized spacers in different areas of the implant site. For example, as shown in the example of FIG. 4, which will be described in further detail later, different sized spacers (e.g., 200a, 200b) can include spacers of different diameters or volumes. In an example where a plurality of spacers are used, a first spacer 200a of the plurality of spacers can include a first diameter, and a second spacer 200b of the plurality of spacers can include a second diameter that is different from the first diameter. One reason a surgeon may use different sized spacers in different locations is to be able to use the fixation material 50 to fill in some of the gap (e.g., FIG. 2E, target thickness 52) between the bone surface 1 and the prosthesis 60 where there is bone loss. The methods and spacers 200 described herein can facilitate a more anatomically correct placement of the prosthesis 60 in relation to the acetabulum 2 and a more desirable fixation material 50 thickness 52.

As described herein, substantially spherical can include spherical-type shapes such as a polyhedron having a substantially spherical form, including, but not limited to a dodecahedron, a spherical polyhedron, and other spherical type shapes. Irregular spacers having substantially spherical type base shapes can also be used.

The spacer 200 can be formed of biocompatible materials such as bone cement, however any suitable biocompatible material can be used to form the spacer 200 such as metals, polymers, ceramics, or the like.

Method 300 can be described as recreating the acetabulum 2. In some examples, recreating the acetabulum is primarily accomplished by the fixation material 50 surface that adjoins the prosthesis, as opposed to the anchor 100 serving as the primary component that recreates the acetabulum. For example, the anchor 100 can serve primarily as an anchor for the layer of fixation material 50, while the fixation material 50 fills in voids and provides the new acetabular surface that supports the prosthesis 60.

In addition to the illustrative example of FIG. 1 previously described, FIGS. 4, 5A, 5B, 6A, 6B, 7A, 7B, 8A and 8B also show example anchors (400a, 400b, 400c, 500, 600, 700 and 800). The features of any of the anchors described herein can be used in any combination, and features can be added or eliminated.

FIG. 4 is a perspective view of another example of illustrative augments that are arranged at an implant site 40 of a hip bone 1, in accordance with at least one example. The anchors 400a, 400b and 400c shown in FIG. 4 can be similar to the anchors 100 shown in FIG. 1 in many respects. However, while the anchors 100 shown in the example of FIG. 1 are generally planar and are depicted with a single hole 130, anchors 400a, 400b and 400c can have a curved shape and can have a plurality of openings 430. Anchors 400a, 400b and 400c can include a body that is shaped to approximate a surface of an acetabulum 2, or is conformable to approximate a portion of a surface of an acetabulum 2.

In some examples, the anchor 400a, 400b and 400c can be tailored to conform to and cover at least a portion of an acetabulum 2 of a particular living being. This can be accomplished using imaging data obtained for the particular living being, and by ordering, selecting or manufacturing an anchor tailored to the particular living being. Manufacturing can be done, for example, by 3D printing. The shape of the anchor 400a, 400b, 400c could also be tailored to the specific living being by manipulating a standard sized anchor 400 by hand or machine, or by selecting from a range of standard sizes, or an average or other mathematical value of a range of sizes. The shape of the anchor can also be formed by taking a sheet of suitable material and trimming or breaking off portions of the material to create the appropriate shape for the application. The material that is trimmed can have openings already extending there through for receiving the fasteners. The material can be trimmed based on the application and the anatomy.

Figure 5A:
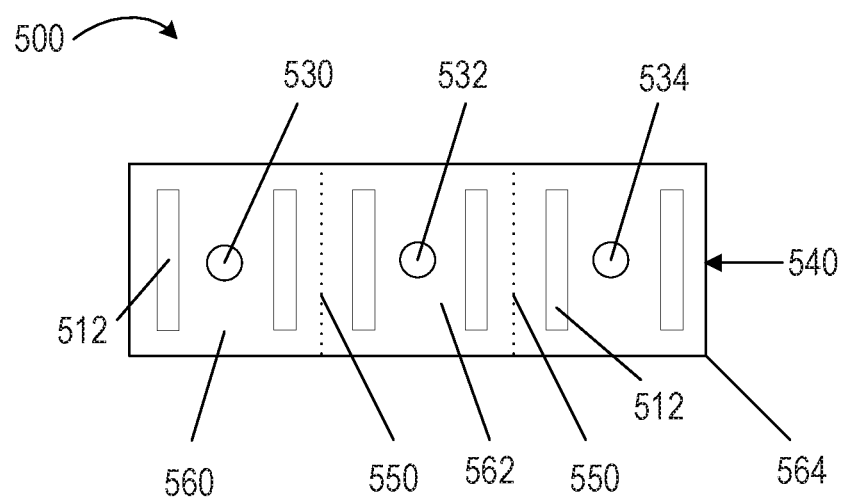
FIGS. 5A and 5B are top and side views of another illustrative augment in the form of an anchor, in accordance with at least one example.
Figure 5B:
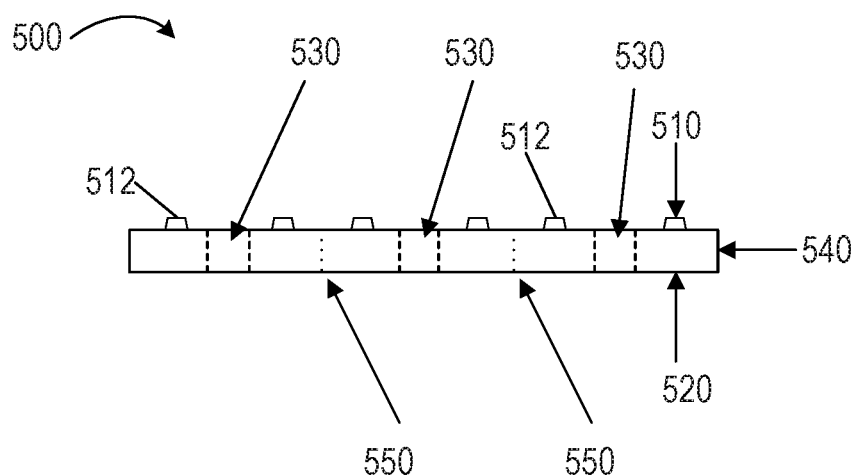

FIGS. 5A and 5B are top and side views of another illustrative augment in the form of an anchor 500, in accordance with at least one example. Like the anchors 400 of FIG. 4, the anchor 500 shown in FIGS. 5A and 5B can also be similar to the anchors 100 of FIG. 1 in many respects.

The anchor 500 can include a body having a first surface 510 and a second surface 520 opposite and spaced apart from the first surface 510 (FIG. 5B). The anchor 500a can also include an opening 530 extending from the first surface 510 to the second surface 520. The opening 530 can be sized and shaped to accept insertion of a fastener 900 (FIG. 9) through the opening 530 so that the fastener 900 can be secured to the bone 1. The fastener 900 can be any fastener, including the example fasteners 900a, 900b and 900c which will be shown and described with reference to FIG. 9.

All or a portion of the anchor 500, and any of the other anchors described herein can be formed of a layer of porous material that promotes boney ingrowth. In some examples, the anchor 500 (or any other anchor) can be formed entirely of a porous material that promotes bone ingrowth. In some examples, both the first surface 510 and the second surface 520 can include the porous material that supports boney ingrowth. In other examples, only one of the first and second surfaces 510, 520 include the porous material that supports boney ingrowth.

In some examples, instead of the anchor being entirely formed of the porous material that promotes boney ingrowth, the anchor 500 can be formed only partially of a porous material that promotes boney ingrowth. For example, the anchor 500 could be formed of a composite of layers, where one of the layers is a solid layer and the porous material is located adjacent to the solid layer on one or more sides. In some examples, the anchor 500 can be formed of the same porous material but with different levels of porosity in different regions of the anchor 500, such as a high porosity at the second surface 520 and a low porosity at the first surface 510. In some examples, there can be a porosity gradient where the porosity is higher at the second surface 520 and decreases towards the first surface 510, or vice-versa.

In some examples, the anchor 500 can be formed having a first surface 510 that includes gripping formations 512 to promote adhesion of the first surface 510 to a fixation material 50 (e.g., 50, FIG. 2E), while the second surface 520 includes the porous material that promotes boney ingrowth for improved attachment to the bone 1. In some examples including examples that incorporate the gripping formation 512, the first surface 510 can be less porous than the second surface 520.

As shown in the example of FIGS. 5A and 5B, the anchor 500 can include a first portion 560 having a first opening 530 and a second portion 562 including a second opening 532. The first and second openings 530, 532 can extend from the first surface 510 to the second surface 520. In the present example, where there is more than one opening 530, 532, 534 in the anchor 500, step 330 of the previously described method 300 (FIG. 3) can further include inserting a second fastener 900 (e.g., FIG. 9) through the second opening 532, and attaching the second fastener 900 to the bone 1 at a second target bone location to secure the second portion 562 of the anchor 500 to the bone 1. An example of the first and second target bone locations can be understood by reference to anchor 400c in FIG. 4 where a plurality of fasteners 900 can attach the anchor 400c to the bone 1.

Also shown in the example of FIG. 5, the anchor 500 can further include one or more bendable hinge portions 550, such as located between a first portion 560 and a second portion 562, or between the second portion 562 and a third portion 564. Likewise, the method 300 can include bending the anchor 500 at one of the hinge portions 550 and attaching two of the portions 560, 562, 564 to multiple target bone locations. In some examples, the hinge portion 550 can be located between the first portion 560 and the second portion 562, or between the opening 530 and the second opening 532. Any number of portions can be provided and the portions can be provided in any shape or arrangement to facilitate anchoring to an acetabulum.

Although the anchor 500 is shown as a rectangular anchor extending in a single direction, the anchor 500 can be formed in an L-shape or even an irregular shape. The hinge portions 550 do not necessarily need to be parallel to one another as shown in the example. The anchor 500 can be formed in complex shapes to match the anatomy of an acetabulum. For example, instead of having generally square first, second and third portions 560, 562, 564 separated by parallel hinge portion 550, the anchor 500 could have triangular or other shaped first, second and third portions 560, 562, 564 and non-parallel hinge portions 550, or any combination thereof.

FIGS. 6A, 6B, 7A, 7B, 8A and 8B show additional embodiments of anchors having a variety of characteristics that can be used in combination or alone with one another, or with any other embodiment.

Figure 6A:
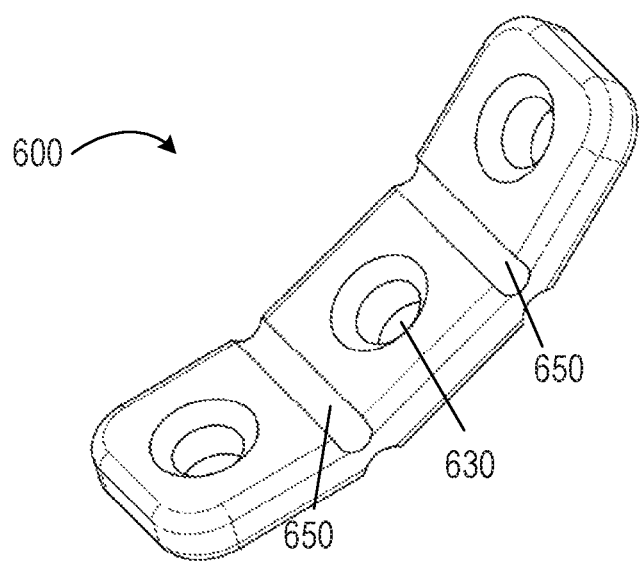
FIGS. 6A and 6B are perspective and side views of another illustrative augment in the form of an anchor, in accordance with at least one example.
Figure 6B:
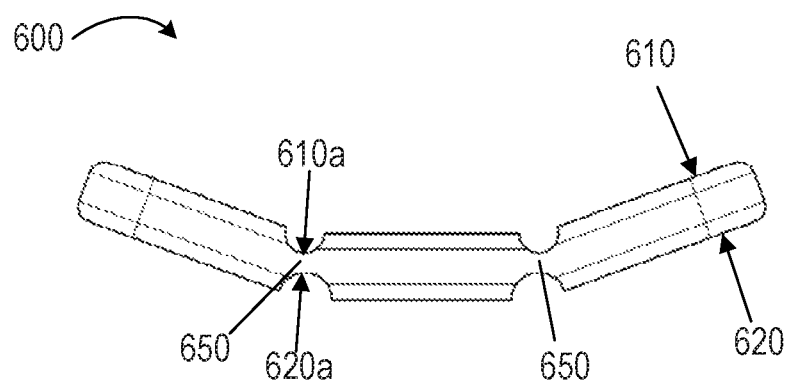

FIGS. 6A and 6B show an anchor 600 similar to the example of FIGS. 5A and 5B. FIGS. 6A and 6B show an illustrative example of hinge portions 650 in the form of living hinges. A general thickness of anchor 600 can be described as a distance from the first surface 610 to the second surface 620, with opening 630 extending therethrough to accept one or more fasteners 900 (e.g., fasteners shown in FIG. 9). The thickness at the hinge portions 650 can be described as a distance extending from a first hinge surface 610a to a second hinge surface 620a. The thickness of the anchor 600 at the hinge portion 650 can be less than the thickness of the anchor 600 in other parts of the anchor 600. In some examples, instead of a difference in thickness, or in addition to a difference in thickness, the material at the hinge portions 650 may include different material characteristics. For example, the hinge portions 650 may be more bendable, ductile, or more susceptible to bending than other portions of the anchor 600.

Figure 7A:
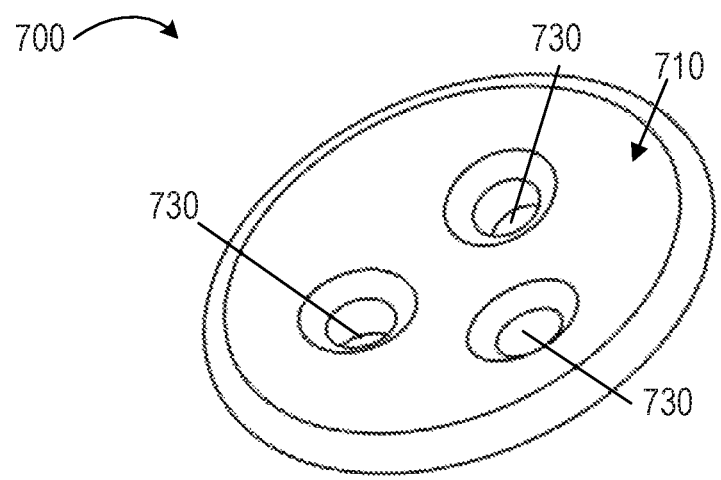
FIGS. 7A and 7B are perspective and side views of another illustrative augment in the form of an anchor, in accordance with at least one example.
Figure 7B:
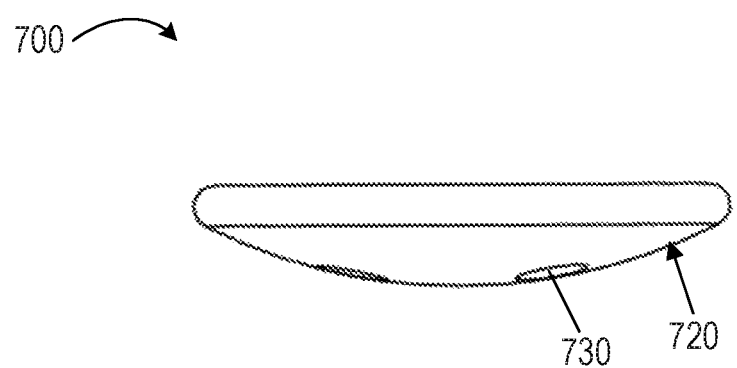

FIGS. 7A and 7B show an example of a curved disk-shaped anchor 700 having one or more openings 730 extending through a body from a first surface 710 to a second surface 720. The openings 730 can be adapted to accept one or more fasteners (e.g., fasteners 900 shown in FIG. 9). The first and/or second surfaces 710, 720 of anchor 700 can be curved to have a consistent radius, or can have a varied curved surfaces to match with the shape of a particular location on a bone or prosthesis.

Figure 8A:
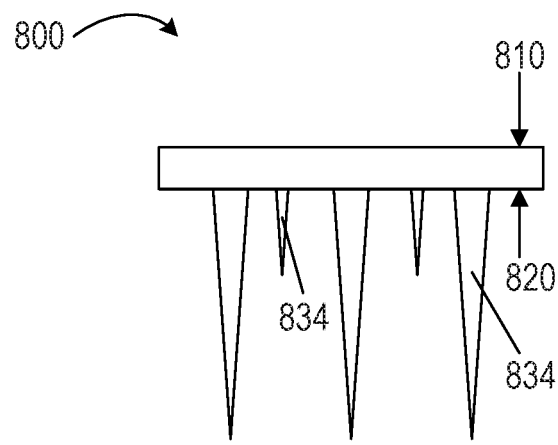
FIGS. 8A and 8B are side and bottom views of another illustrative augment in the form of an anchor, in accordance with at least one example.
Figure 8B:
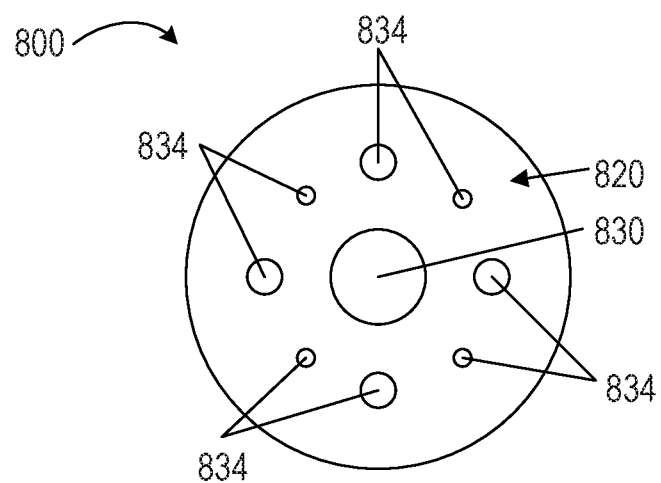
Figure 9:
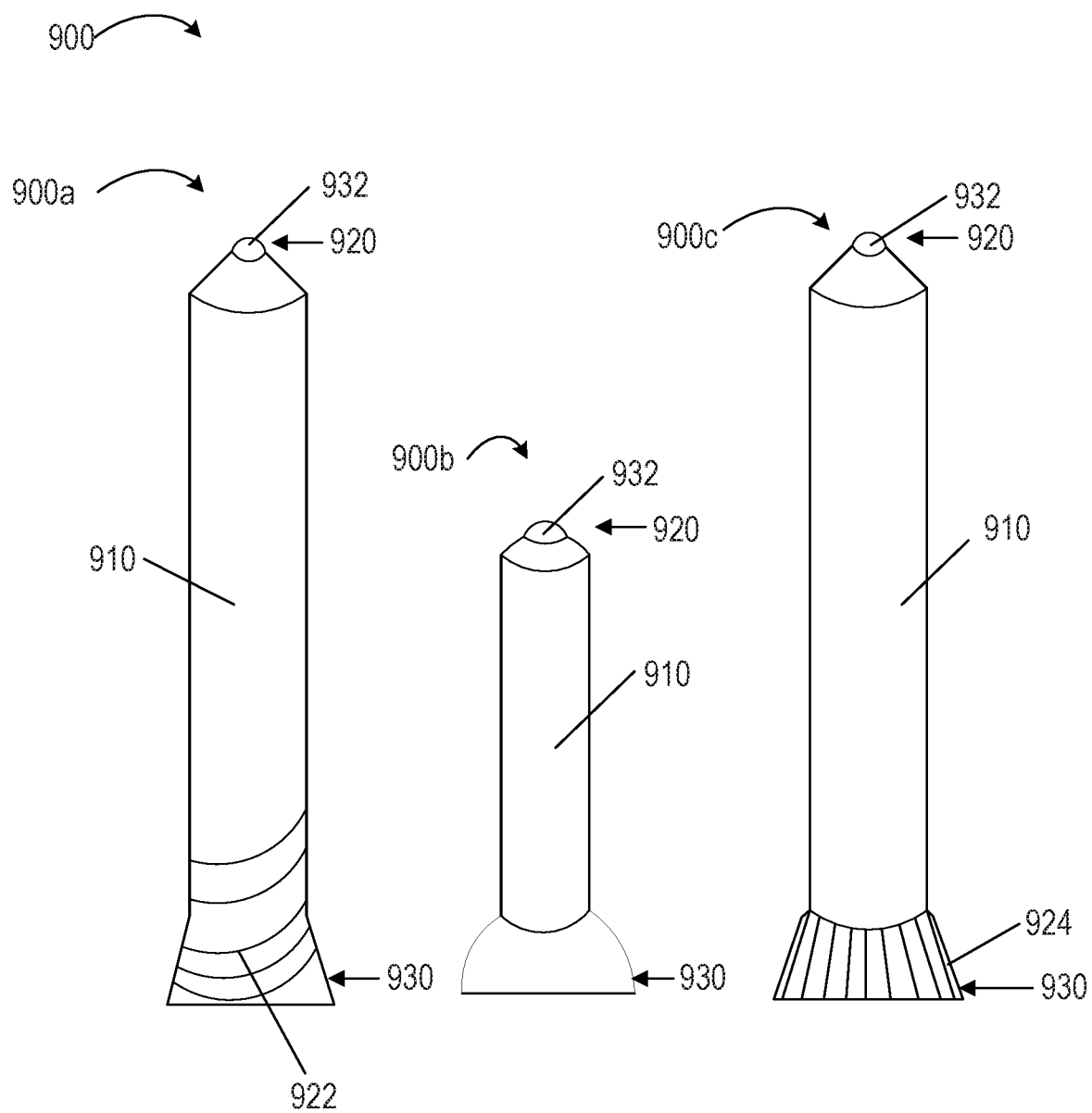
FIG. 9 is a top perspective view of illustrative anchors in the form of fasteners that can be used alone or together with the anchors of FIGS. 1, 4, 5A, 5B, 6A, 6B, 7A, 7B, 8A and 8B, to anchor an orthopedic implant to the bone, in accordance with at least one example.

FIGS. 8A and 8B show an example of an anchor 800 that has a planar disk-shaped body having one or more openings 830 extending through the body from a first surface 810 to a second surface 820 to accept one or more fasteners (e.g., fasteners 900 shown in FIG. 9). The second surface 820 of anchor 800 can include one or more spikes 834 (e.g., protrusions) that can engage with bone when implanted to enhance fixation to the bone 1. The spikes 834 can be of various shapes, sizes and lengths. Conical shaped spikes are shown, but any suitable shape can be provided, including but not limited to: columnar spikes having a blunt or pointed tip, and pyramidal spikes. In some examples, the body and/or the spikes 834 of anchor 800 can be formed of a porous material to promote boney ingrowth. In some examples, the body can include the porous material to promote boney ingrowth, while the spikes 834 are formed of a solid material.

FIG. 9 is a side view of illustrative anchors in the form of fasteners 900a, 900b and 900c that can be used alone or together with any of the anchors 100, 400a, 400b, 400c, 500, 600, 700 and 800 (FIGS. 1, 4, 5A, 5B, 6A, 6B, 7A, 7B and 8) to anchor a prosthesis to a bone, in accordance with at least one example.

The fasteners 900a, 900b and 900c can be formed to include at least a section that has a porous material to promote boney ingrowth. For example, the porous material can be included anywhere along the elongate body 910 of the fastener 900 that extends between a tip 920 and a head 930 of the fastener 900. In some examples the tip 920 and/or head 930 can include less porous, or solid sections. For example, a solid portion 932 can be useful for maintaining integrity of the fastener 900 during insertion. In some examples, a solid head 930 can be useful for attachment to fixation material 50. Various features of the fastener 900 can include threads 922 or buttress formations 924. The threads 922 and buttress formation 924 can act as gripping formations and facilitate better attachment to the bone, and/or better engagement with the fixation material 50 (e.g., FIG. 2E) covering the fasteners 900.

Any of the fasteners 900a, 900b, 900c described in FIG. 9 can be used with the method 300 of FIG. 3. The fastener can be inserted until it is flush with the anchor 100, or the fastener can be inserted such that it is left proud of the anchor 100 to provide additional engagement with the fixation material 50 (FIG. 2E). The fasteners 900a, 900b, 900c of FIG. 9 can also be used alone (e.g., omitting the anchor 100 as shown in FIG. 2E). If the fasteners 900a, 900b, 900c are used alone and as the only anchor, they can be left proud of the bone 1 surface so that when the layer of fixation material 50 (e.g., step 340) is applied over the fastener 900 and the bone 1, a greater surface area of the fastener is engaged with the fixation material 50 to create a surrogate bone surface for the prosthesis 60 to be secured to.

To facilitate boney ingrowth, any of the anchors (100, 400a, 400b, 400c, 500, 600, 700 and 800) of FIGS. 1, 4, 5A, 5B, 6A, 6B, 7A, 7B, 8A and 8B, and the fastener 900 of FIG. 9, can be formed of a three-dimensional structure that supports boney ingrowth. For example, a highly porous, three-dimensional metallic structure can be provided that incorporates one or more of a variety of biocompatible metals such as but not limited to titanium, a titanium alloy, cobalt chromium, cobalt chromium molybdenum, tantalum, a tantalum alloy, niobium, or alloys of tantalum and niobium with one another or with other metals. Such structures are particularly suited for contacting bone and/or soft tissue, and in this regard, can be useful as bone substitutes and other implants and implant components that are receptive to cell and tissue ingrowth, for example, by allowing boney tissue or other tissue to grow into the porous structure over time to enhance fixation (e.g., osseointegration) between the structure and surrounding bodily structures. According to certain examples of the present disclosure, an open porous metal structure, or a portion thereof, can have a bulk porosity as low as 55%, 65%, or 75% or as high as 80%, 85%, or 90%, or within any range defined between any pair of the foregoing values, and in this regard, such structures can provide lightweight, yet strong porous implants. Certain porous metal structures, despite having such high porosities, are capable of withstanding extreme mechanical loads at the time of implantation and over long periods of time, for example, where a highly porous, three-dimensional metallic structure is forcefully impacted and press fit into a bone, by itself or connected to another implant, and maintains its shape during impaction and following many months or years of service in the body. Such structures can be manufactured according to any suitable technique or process. An example of an open porous metal structure is produced using Trabecular Metal™ Technology available from Zimmer, Inc., of Warsaw, Ind. Trabecular Metal™ is a trademark of Zimmer, Inc. Such a material can be formed from a reticulated vitreous carbon foam substrate which is infiltrated and coated with a biocompatible metal, such as tantalum, by a chemical vapor deposition ("CVD") process in the manner disclosed in detail in U.S. Pat. No. 5,282,861 and in Levine, B. R., et al., "Experimental and Clinical Performance of Porous Tantalum in Orthopedic Surgery", Biomaterials 27 (2006) 4671-4681, the disclosures of which are expressly incorporated herein by reference.

In some instances, a highly porous, three-dimensional metallic structure will be fabricated using a selective laser sintering (SLS) or other additive manufacturing-type process such as direct metal laser sintering or electron beam melting. In one example, a three-dimensional porous article is produced in layer-wise fashion from a laser-fusible powder, e.g., a single-component metal powder, which is deposited one layer at a time. The powder is fused, remelted or sintered, by the application of laser energy that is directed to portions of the powder layer corresponding to a cross section of the article. After the fusing of the powder in each layer, an additional layer of powder is deposited, and a further fusing step is carried out, with fused portions or lateral layers fusing so as to fuse portions of previous laid layers until a three-dimensional article is complete. In certain examples, a laser selectively fuses powdered material by scanning cross-sections generated from a 3-D digital description of the article, e.g., from a CAD file or scan data, on the surface of a powder bed. Complex geometries can be created using such techniques, and in some instances, net shape and near net shape implants are constructed. In some examples, a non-porous or essentially non-porous base substrate will provide a foundation upon which a three-dimensional porous structure will be built and fused thereto using a selective laser sintering (SLS) or other additive manufacturing-type process. Such substrates can incorporate one or more of a variety of biocompatible metals such as any of those disclosed herein.

Generally, a highly porous, three-dimensional metallic structure will include a large plurality of ligaments that define open voids (e.g., pores) or channels between the ligaments. The open spaces between the ligaments form a matrix of continuous channels having few or no dead ends, such that growth of soft tissue and/or bone through the open porous metal is substantially uninhibited. According to some aspects of the present disclosure, exterior surfaces of an open porous metal structure can feature terminating ends of the above-described ligaments. Such terminating ends can be referred to as struts, and they can generate a high coefficient of friction along an exposed porous metal surface. Such features can impart an enhanced affixation ability to an exposed porous metal surface for adhering to bone and soft tissue. Also, when such highly porous metal structures are coupled to an underlying substrate, a small percentage of the substrate can be in direct contact with the ligaments of the highly porous structure, for example, approximately 15%, 20%, or 25%, of the surface area of the substrate can be in direct contact with the ligaments of the highly porous structure.

A highly porous, three-dimensional metallic structure can be fabricated such that it comprises a variety of densities in order to selectively tailor the structure for particular orthopedic applications, for example, by matching the structure to surrounding natural tissue in order to provide an improved matrix for tissue ingrowth and mineralization. Such structures can be isotropic or anisotropic. In this regard, according to certain examples, an open porous metal structure can be fabricated to have a substantially uniform porosity, density, void (pore) size, pore shape, and/or pore orientation throughout, or to have one or more features such as porosity, density, void (pore) size, pore shape, and/or pore orientation being varied within the structure, or within a portion thereof. For example, an open porous metal structure can have a different pore size, pore shape, and/or porosity at different regions, layers, and surfaces of the structure. The ability to selectively tailor the structural properties of the open porous metal enables, for example, tailoring of the structure for distributing stress loads throughout the surrounding tissue and promoting specific tissue ingrown within the open porous metal. In some instances, a highly porous, three-dimensional metallic structure, once formed, will be infiltrated and coated with one or more coating materials such as biocompatible metals such as any of those disclosed herein.

In some examples, the porous metal structure can be a formed from a titanium alloy using an additive manufacturing process, such as with OsseoTi™, which is commercially available from Biomet Manufacturing, LLC (Warsaw, Ind., USA). Briefly, however, OsseoTi™ is highly biocompatible, has high corrosion resistance and includes a highly interconnected porous architecture that mimics the porous structure of human cancellous bone, which can enhance bone integration and in-growth. In one exemplary implementation, OsseoTi™ can include a porous construct with a porosity.

Figure 10:
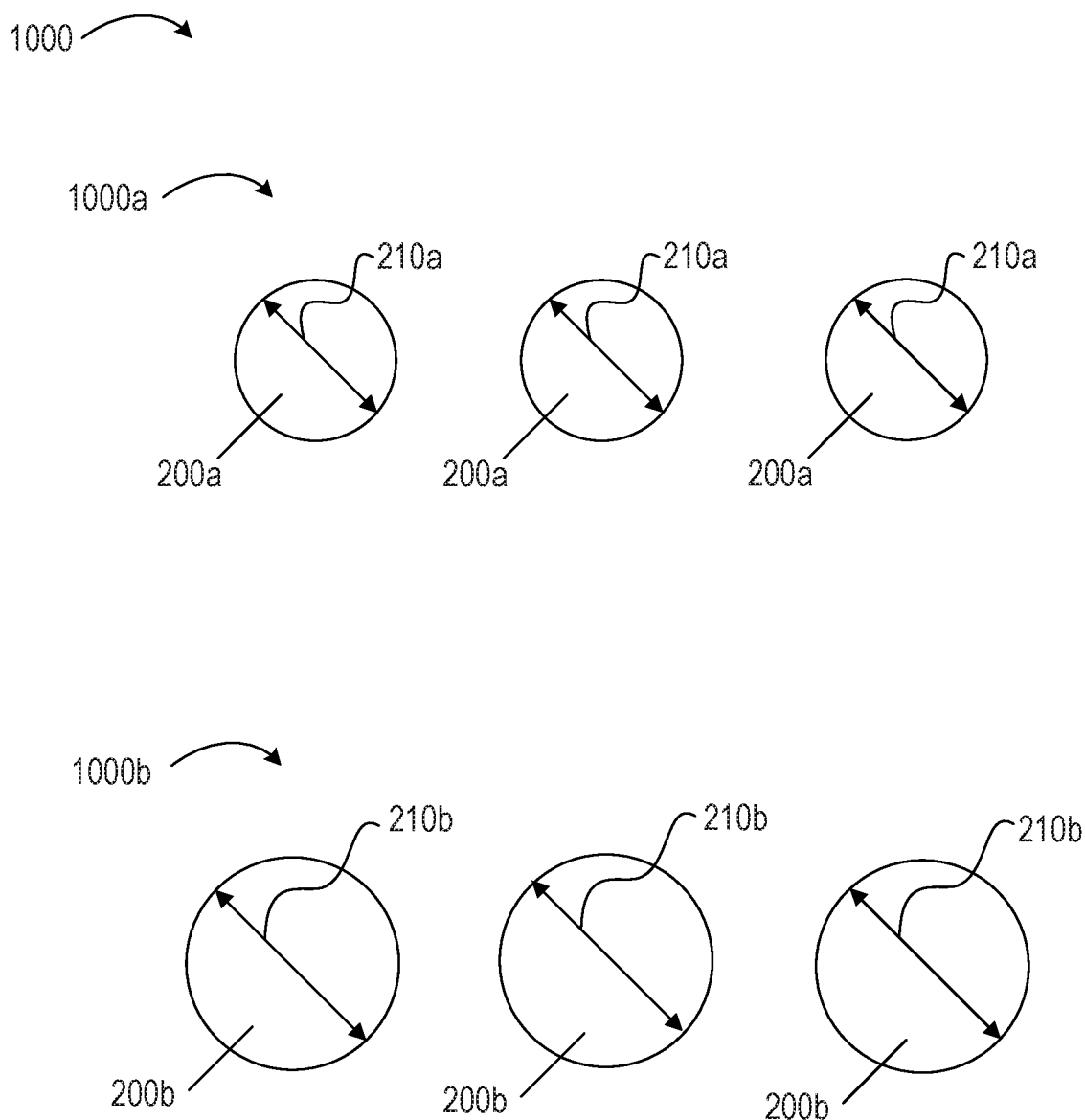
FIG. 10 depicts an illustrative system of augments in the form of spacers for controlling and adjusting fixation material thickness during implantation of a prosthesis, in accordance with at least one example.

FIG. 10 depicts an illustrative system 1000 for controlling/adjusting a fixation material thickness during implantation of a cup or shell of a prosthesis, in accordance with at least one example. The benefit of the system 1000 of FIG. 10 is that it provides the ability to control and adjust fixation material 50 thickness 52 as shown in FIG. 2E. The system 1000 can include a first set 1000a of three or more first spacers 200a formed of a biocompatible material such as a bone cement material. The first set 1000a of three or more first spacers 200a can have a generally spherical shape as previously described, having a first diameter 210a that is sized to control the target thickness 52 of the fixation material 50 (FIG. 2E) that supports the orthopedic hip prosthesis 60 to a first target thickness. In some examples, the first set 1000a of three or more first spacers 200a are inserted into or embedded in the fixation material 50 (e.g., FIG. 2D). The spacers 200a being implanted before the shell or cup of the prosthesis 60 (e.g., FIG. 2E). When the prosthesis 60 is implanted, the spacers may be located in a gap (e.g., FIG. 2E, 52) between the bone 1 and the prosthesis 60. This gap can be approximated as the distance between the prosthesis 60 and the bone 1.

In some examples, the system 1000 can also include a second set 1000b of three or more second spacers 200b that can be used in the same manner described for the first spacers 200a. The second set of spacers 1000b can have a generally spherical shape and a second diameter 210b sized to control a target thickness 52 of a fixation material 50 that supports the prosthesis 60 to a second target thickness. The second diameter 210b can be different from the first diameter 210a in order to provide the surgeon more options for controlling and adjusting the fixation material 50 thickness.

In some methods, the surgeon may want to select and use only spacers 200a, 200b from the first set 1000a or the second set 1000b. In other methods, the surgeon may want to select and use a combination of spacers 200a, 200b from different sets (1000a, 1000b, etc.) having different diameters 210a, 210b. This added customizability allows the surgeon to better tailor the fixation material 50 target thickness 52 to the needs of the particular living being.

The above detailed description includes references to the accompanying drawings, which form a part of the detailed description. The drawings show, by way of illustration, specific examples in which the invention can be practiced. These examples are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) can be used in combination with each other. Other examples can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed example. Thus, the following claims are hereby incorporated into the Detailed Description as examples or examples, with each claim standing on its own as a separate example, and it is contemplated that such examples can be combined with each other in various combinations or permutations. The scope of the invention should be determined with reference to the appended claims, along with the full scope of equivalents to which such claims are entitled.

VARIOUS NOTES AND EXAMPLES

To better illustrate the devices and methods disclosed herein, a non-limiting list of embodiments is provided herein.

Example 1 is a method of anchoring an orthopedic hip prosthesis including a shell or a cup to an acetabulum of a living being, the method comprising: placing an augment at a bone surface of the acetabulum; applying a layer of fixation material over the bone surface in an amount sufficient to cover the augment; and implanting the prosthesis over the layer of fixation material to secure the prosthesis to the layer of fixation material.

In Example 2, the subject matter of Example 1 optionally includes wherein the augment is an anchor having a body including a first surface opposite a second surface and an opening extending through the body from the first surface to the second surface, the method further including: identifying a target bone location; inserting a fastener through the opening; and attaching the fastener to the target bone location to secure the anchor to the acetabulum, wherein after attaching the fastener to the target bone location, applying the layer of fixation material includes covering the anchor and the bone surface with the layer of fixation material, wherein the layer of fixation material forms a surrogate bone surface for the target bone location and bone surrounding the target bone location to support the prosthesis.

In Example 3, the subject matter of Example 2 optionally includes wherein the anchor is formed of a layer of porous material that promotes boney ingrowth, and the layer of porous material is shaped to cover a portion of the acetabulum.

In Example 4, the subject matter of any one or more of Examples 2-3 optionally include wherein the anchor includes a porous material that promotes boney ingrowth and the anchor is generally planar in shape.

In Example 5, the subject matter of any one or more of Examples 2-4 optionally include wherein the anchor includes a first portion having the opening and a second portion including a second opening, the second opening extending from the first surface to the second surface, the method further including inserting a second fastener through the second opening, and attaching the second fastener to the acetabulum at a second target bone location to secure the second portion of the anchor to the bone.

In Example 6, the subject matter of Example 5 optionally includes wherein the augment includes a hinge portion located between the first portion and the second portion, and the method further includes bending the augment at the hinge portion before anchoring the second portion to the second target bone location.

In Example 7, the subject matter of any one or more of Examples 1-6 optionally include wherein placing an augment at a bone surface includes placing three or more substantially spherical spacers at the bone surface after applying the layer of fixation material to the bone surface, and wherein placing the three or more substantially spherical spacers includes inserting the three or more spacers into the layer of fixation material in a triangular arrangement, the method further including pressing the prosthesis into the layer of fixation material until the prosthesis bottoms out on the three or more substantially spherical spacers.

In Example 8, the subject matter of Example 7 optionally includes wherein the layer of fixation material is a bone cement and wherein a presence of the three or more substantially spherical spacers in the bone cement controls a target thickness of the bone cement that supports the prosthesis.

In Example 9, the subject matter of Example 8 optionally includes wherein the target thickness of the bone cement is variable along the acetabulum.

In Example 10, the subject matter of any one or more of Examples 8-9 optionally include wherein a first spacer of the three or more spacers includes a first diameter, and a second spacer of the three or more spacers includes a second diameter that is different than the first diameter.

In Example 11, the subject matter of any one or more of Examples 1-10 optionally include wherein the augment is a substantially spherical spacer, and wherein placing the augment at the bone surface includes inserting a plurality of the substantially spherical spacer into the layer of fixation material after applying the layer of fixation material, and wherein implanting the prosthesis includes applying a force to the prosthesis to push the prosthesis into the layer of fixation material until the prosthesis bottoms out on the plurality of spacers.

In Example 12, the subject matter of Example 11 optionally includes wherein the plurality of the substantially spherical spacers includes three or more substantially spherical spacers, and wherein placing the plurality of spacers at the bone surface includes placing the plurality of spacers in a triangular arrangement.

In Example 13, the subject matter of Example 12 optionally includes wherein the layer of fixation material is a bone cement and wherein a presence of the plurality of spacers in the layer of fixation material controls a thickness of the layer of fixation material that supports the prosthesis.

In Example 14, the subject matter of Example 13 optionally includes wherein a target thickness of the bone cement corresponds to a diameter of the spacers.

Example 15 is a system for controlling fixation material thickness during implantation of an orthopedic hip prosthesis to an acetabulum of a living being, the system comprising: a set of three or more first spacers formed of a biocompatible material, the set of three or more first spacers having a generally spherical shape and a first diameter sized to control a target thickness of a fixation material that supports the orthopedic hip prosthesis when the set of three or more first spacers are embedded in the fixation material, wherein the fixation material occupies a gap between the orthopedic hip prosthesis and the acetabulum.

In Example 16, the subject matter of Example 15 optionally includes a second set of three or more second spacers, the set of second spacers having a generally spherical shape and a second diameter sized to control a target thickness of a fixation material that supports the orthopedic hip prosthesis when implanted, wherein the second diameter is different from the first diameter.

In Example 17, the subject matter of any one or more of Examples 15-16 optionally include wherein the set of three or more spacers, and the second set of three or more spacers are formed of a bone cement material.

Example 18 is an anchor for placement between a shell or cup of an orthopedic hip prosthesis and an acetabulum of a living being, the anchor comprising: a body having a first surface and a second surface opposite and spaced apart from the first surface, the body including a porous material that promotes boney ingrowth; and an opening extending from the first surface to the second surface, the opening sized and shaped to accept insertion of a fastener through the opening to be secured to the acetabulum.

In Example 19, the subject matter of Example 18 optionally includes wherein the first surface includes gripping formations to promote adhesion of the first surface to a fixation material, and the second surface includes the porous material that promotes boney ingrowth, and wherein the first surface is less porous than the second surface.

In Example 20, the subject matter of any one or more of Examples 18-19 optionally include wherein both the first surface and the second surface include the porous material that promotes boney ingrowth.

In Example 21, the subject matter of any one or more of Examples 18-20 optionally include wherein the body is a layer of porous material that supports boney ingrowth and is conformable to approximate a surface of an acetabulum of the living being.

In Example 22, the subject matter of Example 21 optionally includes wherein the body includes a first portion having the opening and a second portion including a second opening, the second opening extending from the first surface to the second surface, the anchor further comprising a hinge portion located between the first portion and the second portion, and wherein the anchor is bendable at the hinge portion.

What is claimed is:

1. A method of anchoring an orthopedic hip prosthesis including a shell or a cup to an acetabulum of a living being, the method comprising:
    placing an augment at a bone surface of the acetabulum, wherein the augment is an anchor having a body including a first surface opposite a second surface and an opening extending through the body from the first surface to the second surface, the method further including;
    applying a layer of fixation material over the bone surface in an amount sufficient to cover the augment; and
    implanting the prosthesis over the layer of fixation material to secure the prosthesis to the layer of fixation material,
    the method further including:
        identifying a target bone location;
        inserting a fastener through the opening;
        attaching the fastener to the target bone location to secure the anchor to the acetabulum, wherein after attaching the fastener to the target bone location, applying the layer of fixation material includes covering the anchor and the bone surface with the layer of fixation material, wherein the layer of fixation material forms a surrogate bone surface for the target bone location and bone surrounding the target bone location to support the prosthesis; and
        placing three or more substantially spherical spacers at the bone surface after applying the layer of fixation material to the bone surface, and wherein placing the three or more substantially spherical spacers includes inserting the three or more spacers into the layer of fixation material in a triangular arrangement, the method further including pressing the prosthesis into the layer of fixation material until the prosthesis bottoms out on the three or more substantially spherical spacers, and
    wherein the layer of fixation material is a bone cement and wherein a presence of the three or more substantially spherical spacers in the bone cement controls a target thickness of the bone cement that supports the prosthesis.

2. The method of claim 1, wherein the anchor is formed of a layer of porous material that promotes boney ingrowth, and the layer of porous material is shaped to cover a portion of the acetabulum.

3. The method of claim 1, wherein the anchor includes a porous material that promotes boney ingrowth and the anchor is generally planar in shape.

4. The method of claim 1, wherein the anchor includes a first portion having the opening and a second portion including a second opening, the second opening extending from the first surface to the second surface, the method further including inserting a second fastener through the second opening, and attaching the second fastener to the acetabulum at a second target bone location to secure the second portion of the anchor to the bone.

5. The method of claim 4, wherein the augment includes a hinge portion located between the first portion and the second portion, and the method further includes bending the augment at the hinge portion before anchoring the second portion to the second target bone location.

6. The method of claim 1, wherein the target thickness of the bone cement is variable along the acetabulum.

7. The method of claim 1, wherein a first spacer of the three or more spacers includes a first diameter, and a second spacer of the three or more spacers includes a second diameter that is different than the first diameter.

* * * * *